US008444844B1

(12) United States Patent
Teamey et al.

(10) Patent No.: US 8,444,844 B1
(45) Date of Patent: May 21, 2013

(54) ELECTROCHEMICAL CO-PRODUCTION OF A GLYCOL AND AN ALKENE EMPLOYING RECYCLED HALIDE

(71) Applicant: Liquid Light, Inc., Monmouth Junction, NJ (US)

(72) Inventors: Kyle Teamey, Washington, DC (US); Jerry J. Kaczur, North Miami Beach, FL (US); Emily Barton Cole, Houston, TX (US)

(73) Assignee: Liquid Light, Inc., Monmouth Junction, NJ (US)

( * ) Notice: Subject to any disclaimer, the term of this patent is extended or adjusted under 35 U.S.C. 154(b) by 0 days.

(21) Appl. No.: 13/724,768

(22) Filed: Dec. 21, 2012

Related U.S. Application Data

(60) Provisional application No. 61/703,187, filed on Sep. 19, 2012, provisional application No. 61/720,670, filed on Oct. 31, 2012, provisional application No. 61/675,938, filed on Jul. 26, 2012, provisional application No. 61/703,229, filed on Sep. 19, 2012, provisional application No. 61/703,158, filed on Sep. 19, 2012, provisional application No. 61/703,175, filed on Sep. 19, 2012, provisional application No. 61/703,231, filed on Sep. 19, 2012, provisional application No. 61/703,232, filed on Sep. 19, 2012, provisional application No. 61/703,234, filed on Sep. 19, 2012, provisional application No. 61/703,238, filed on Sep. 19, 2012.

(51) Int. Cl.
*C25B 3/10* (2006.01)
*C07C 55/06* (2006.01)

(52) U.S. Cl.
USPC .......................... 205/440; 562/597; 568/874

(58) Field of Classification Search
USPC .......................................... 562/597; 568/874
See application file for complete search history.

(56) References Cited

U.S. PATENT DOCUMENTS

| | | |
|---|---|---|
| 3,293,292 A | 12/1966 | Olivier et al. |
| 3,326,998 A | 6/1967 | Reusser et al. |
| 3,341,615 A | 9/1967 | Wulf et al. |
| 3,341,616 A | 9/1967 | Vives |
| 3,352,935 A | 11/1967 | Mahan |
| 3,361,653 A | 1/1968 | Miller |
| 3,492,209 A | 1/1970 | Miller |
| 3,720,591 A | 3/1973 | Skarlos |
| 4,087,470 A | 5/1978 | Suzuki |
| 4,162,948 A | 7/1979 | Yagii et al. |
| 4,245,114 A | 1/1981 | Peltzman |
| 4,256,550 A | 3/1981 | Niinobe et al. |
| 4,381,978 A | 5/1983 | Gratzel et al. |
| 4,523,981 A | 6/1985 | Ang et al. |
| 4,547,271 A | 10/1985 | Bharucha et al. |
| 4,595,465 A | 6/1986 | Ang et al. |
| 4,608,132 A | 8/1986 | Sammells |
| 4,608,133 A | 8/1986 | Morduchowitz et al. |
| 4,673,473 A | 6/1987 | Ang et al. |
| 4,732,655 A | 3/1988 | Morduchowitz et al. |
| 4,968,393 A | 11/1990 | Mazur et al. |
| 5,074,974 A | 12/1991 | Toomey, Jr. |
| 5,107,040 A | 4/1992 | Repman et al. |
| 5,155,256 A | 10/1992 | Chapman |
| 5,412,150 A | 5/1995 | Wessel |
| 5,654,493 A | 8/1997 | Wessel |
| 5,804,045 A | 9/1998 | Orillon et al. |
| 6,380,446 B1 | 4/2002 | Drew et al. |
| 6,465,699 B1 | 10/2002 | Grosso |
| 7,462,752 B2 | 12/2008 | Fong et al. |
| 2002/0022753 A1 | 2/2002 | Drew et al. |
| 2008/0314758 A1 | 12/2008 | Grosso |
| 2010/0191024 A1 | 7/2010 | Uenveren et al. |
| 2010/0270167 A1 | 10/2010 | McFarland |
| 2010/0330435 A1 | 12/2010 | Nemeth et al. |
| 2011/0114501 A1 | 5/2011 | Teamey et al. |
| 2011/0114502 A1 | 5/2011 | Cole et al. |
| 2011/0237830 A1 | 9/2011 | Masel |
| 2012/0004448 A1 | 1/2012 | Bhattacharyya et al. |
| 2012/0004449 A1 | 1/2012 | Bhattacharyya et al. |
| 2012/0004454 A1 | 1/2012 | Bhattacharyya et al. |
| 2012/0215034 A1 | 8/2012 | McFarland |

FOREIGN PATENT DOCUMENTS

| | | |
|---|---|---|
| CA | 1146120 A1 | 5/1983 |
| CA | 1272161 A1 | 7/1990 |
| CA | 2043256 A1 | 12/1991 |
| CA | 2391938 A1 | 5/2001 |
| GB | 1096847 A | 12/1967 |
| GB | 1584524 A | 4/1977 |
| GB | 2038335 A | 7/1980 |
| GB | 2312218 A | 10/1997 |
| WO | WO0138275 A1 | 5/2001 |

OTHER PUBLICATIONS

B. Eneau-Innocent et al., Electroreduction of carbon dioxide at a lead electrode in propylene carbonate: A spectroscopic study, Applied Catalysis B: Environmental 98 (2010) 65-71.
Kotaro Ogura et al., Selective Conversion of CO2 to Ethylene by the Electrolysis at a Three-Phase (Gas/Liquid/Solid) Interface in an Acidic Solution Containing Cupric Ions, Fuel Chemistry Division Preprints 2003, 48(1), 264.
S. Gambino and G. Silvestri, On the electrochemical reduction of carbon dioxide and ethylene, Tetrahedron Letters No. 32, pp. 3025-3028, 1973, Pergamon Press, Printed in Great Britain.
K.S. Udupa, G.S. Subramanian, and H.V.K. UDUPA, The electrolytic reduction of carbon dioxide to formic acid, Electrochimica Acta, 1971, vol. 16, pp. 1593 to 1598, Pergamon Press, Printed in Northern Ireland.
Eggins, Brown, McNeill, and Grimshaw, Carbon Dioxide Fixation by Electrochemical Reduction in Water to Oxalate and Glyoxylate, Tetrahedron Letters vol. 29, No. 8, pp. 945-948, 1988, Pergamon Journals Ltd., Printed in Great Britain.
M. Alvarez-Guerra et al., Conversion of carbon dioxide into formate using a continuous electrochemical reduction process in a lead cathode, Chem. Eng. J. (2012), http://dx.doi.org/10.1016/j.cej.2012.06.099.
Afroza Begum, Electrochemical CO2 Reduction, Thesis, 2011, University of Newfoundland, http://collections.mun.ca/cdm4/document.php?CISOROOT=/theses5&CISOPTR=14718&REC=7.
Satoshi Kaneco, Kenji Iiba, Nobu-Hiide Hiei, Kiyohisa Ohta, Takayuki Mizuno, and Tohru Suzuki, Electrochemical reduction of carbon dioxide to ethylene with high Faradaic efficiency at a Cu electrode in CsOH/ methanol, Electrochimica Acta 44 (1999) 4701-4706.
Keith Scott, A Preliminary Investigation of the Simultaneous Anodic and Cathodic Production of Glyoxylic Acid, Electrochimica Acta, vol. 36, No. 9, pp. 1447-1452, 1991, Printed in Great Britain.

*Primary Examiner* — Elvis O Price
(74) *Attorney, Agent, or Firm* — Suiter Swantz pc llo (57) ABSTRACT

The present disclosure is a method and system for electrochemically co-producing a first product and a second product. The system may include a first electrochemical cell, a first reactor, a second electrochemical cell, at least one second reactor, and at least one third reactor. The method and system for for co-producing a first product and a second product may include co-producing a glycol and an alkene employing a recycled halide.

20 Claims, 4 Drawing Sheets

ELECTROCHEMICAL CO-PRODUCTION OF A GLYCOL AND AN ALKENE EMPLOYING RECYCLED HALIDE

CROSS REFERENCE TO RELATED APPLICATIONS

The present application claims the benefit under 35 U.S.C. §119(e) of U.S. Provisional Application Ser. No. 61/720,670 filed Oct. 31, 2012, U.S. Provisional Application Ser. No. 61/703,187 filed Sep. 19, 2012 and U.S. Provisional Application Ser. No. 61/675,938 filed Jul. 26, 2012. Said U.S. Provisional Application Ser. No. 61/720,670 filed Oct. 31, 2012, U.S. Provisional Application Ser. No. 61/703,187 filed Sep. 19, 2012 and U.S. Provisional Application Ser. No. 61/675,938 filed Jul. 26, 2012 are incorporated by reference in their entireties.

The present application also claims the benefit under 35 U.S.C. §119(e) of U.S. Provisional Application Ser. No. 61/703,229 filed Sep. 19, 2012, U.S. Provisional Application Ser. No. 61/703,158 filed Sep. 19, 2012, U.S. Provisional Application Ser. No. 61/703,175 filed Sep. 19, 2012, U.S. Provisional Application Ser. No. 61/703,231 filed Sep. 19, 2012, U.S. Provisional Application Ser. No. 61/703,232 filed Sep. 19, 2012, U.S. Provisional Application Ser. No. 61/703, 234 filed Sep. 19, 2012, U.S. Provisional Application Ser. No. 61/703,238 filed Sep. 19, 2012. The U.S. Provisional Application Ser. No. 61/703,229 filed Sep. 19, 2012, U.S. Provisional Application Ser. No. 61/703,158 filed Sep. 19, 2012, U.S. Provisional Application Ser. No. 61/703,175 filed Sep. 19, 2012, U.S. Provisional Application Ser. No. 61/703,231 filed Sep. 19, 2012, U.S. Provisional Application Ser. No. 61/703,232 filed Sep. 19, 2012, U.S. Provisional Application Ser. No. 61/703,234 filed Sep. 19, 2012 and U.S. Provisional Application Ser. No. 61/703,238 filed Sep. 19, 2012 are hereby incorporated by reference in their entireties.

The present application incorporates by reference co-pending U.S. patent application Ser. No. 13/724,339, U.S. patent application Ser. No. 13/724,878, U.S. patent application Ser. No. 13/724,647, U.S. patent application Ser. No. 13/724,231, U.S. patent application Ser. No. 13/724,807, U.S. patent application Ser. No. 13/724,996, U.S. patent application Ser. No. 13/724,719, and U.S. patent application Ser. No. 13/724,082 in their entireties.

TECHNICAL FIELD

The present disclosure generally relates to the field of electrochemical reactions, and more particularly to methods and/or systems for electrochemical co-production of a glycol and an alkene employing a recycled reactant.

BACKGROUND

The combustion of fossil fuels in activities such as electricity generation, transportation, and manufacturing produces billions of tons of carbon dioxide annually. Research since the 1970s indicates increasing concentrations of carbon dioxide in the atmosphere may be responsible for altering the Earth's climate, changing the pH of the ocean and other potentially damaging effects. Countries around the world, including the United States, are seeking ways to mitigate emissions of carbon dioxide.

A mechanism for mitigating emissions is to convert carbon dioxide into economically valuable materials such as fuels and industrial chemicals. If the carbon dioxide is converted using energy from renewable sources, both mitigation of carbon dioxide emissions and conversion of renewable energy into a chemical form that can be stored for later use will be possible.

SUMMARY OF THE PREFERRED EMBODIMENTS

The present disclosure includes a system and method for electrochemically co-producing a first product and a second product. The system may include a first electrochemical cell, a first reactor, a second electrochemical cell, at least one second reactor, and at least one third reactor. The method and system for co-producing a first product and a second product may include co-producing a glycol and an alkene employing a recycled halide.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the present disclosure may be better understood by those skilled in the art by reference to the accompanying figures in which.

DETAILED DESCRIPTION

Reference will now be made in detail to the subject matter disclosed, which is illustrated in the accompanying drawings.

The present disclosure includes a system and method for electrochemically co-producing a first product and a second product. The system may include a first electrochemical cell, a first reactor, a second electrochemical cell, at least one second reactor, and at least one third reactor. The method and system for co-producing a first product and a second product may include co-producing a glycol and an alkene employing a recycled halide. In one embodiment, the system may co-produce monoethylene glycol (MEG) and ethylene. An overall equation for the desired reaction is:

$$2CO_2 + 5C_2H_6 \rightarrow C_2H_4(OH)_2 + 5C_2H_4 + 2H_2O.$$

In an advantageous aspect of the present disclosure, chemicals may be co-produced at both the anode and the cathode of each electrochemical cell. The cathode may be used to reduce carbon dioxide to carbon-containing chemicals. The anode may be used to make an oxidation product for subsequent employment in producing another carbon compound. By co-producing chemicals, the overall energy requirement for making each chemical may be reduced by 50% or more. In addition, the cell may be capable of simultaneously making two or more products with high selectivity. In another advantageous aspect of the present disclosure, carbon dioxide may act to oxidize organic compounds, and the organic compounds may act to reduce carbon dioxide. The organic compound, such as ethane, may be the sole source of hydrogen used in the reduction of carbon dioxide. Halogens utilized to couple the oxidation of organics to the reduction of carbon dioxide may be recycled in the process.

Before any embodiments of the disclosure are explained in detail, it is to be understood that the embodiments may not be limited in application per the details of the structure or the function as set forth in the following descriptions or illustrated in the figures. Different embodiments may be capable of being practiced or carried out in various ways. Also, it is to be understood that the phraseology and terminology used herein is for the purpose of description and should not be regarded as limiting. The use of terms such as "including," "comprising," or "having" and variations thereof herein are generally meant to encompass the item listed thereafter and equivalents thereof as well as additional items. Further, unless otherwise noted, technical terms may be used according to conventional usage. It is further contemplated that like reference numbers may describe similar components and the equivalents thereof.

Figure 1:
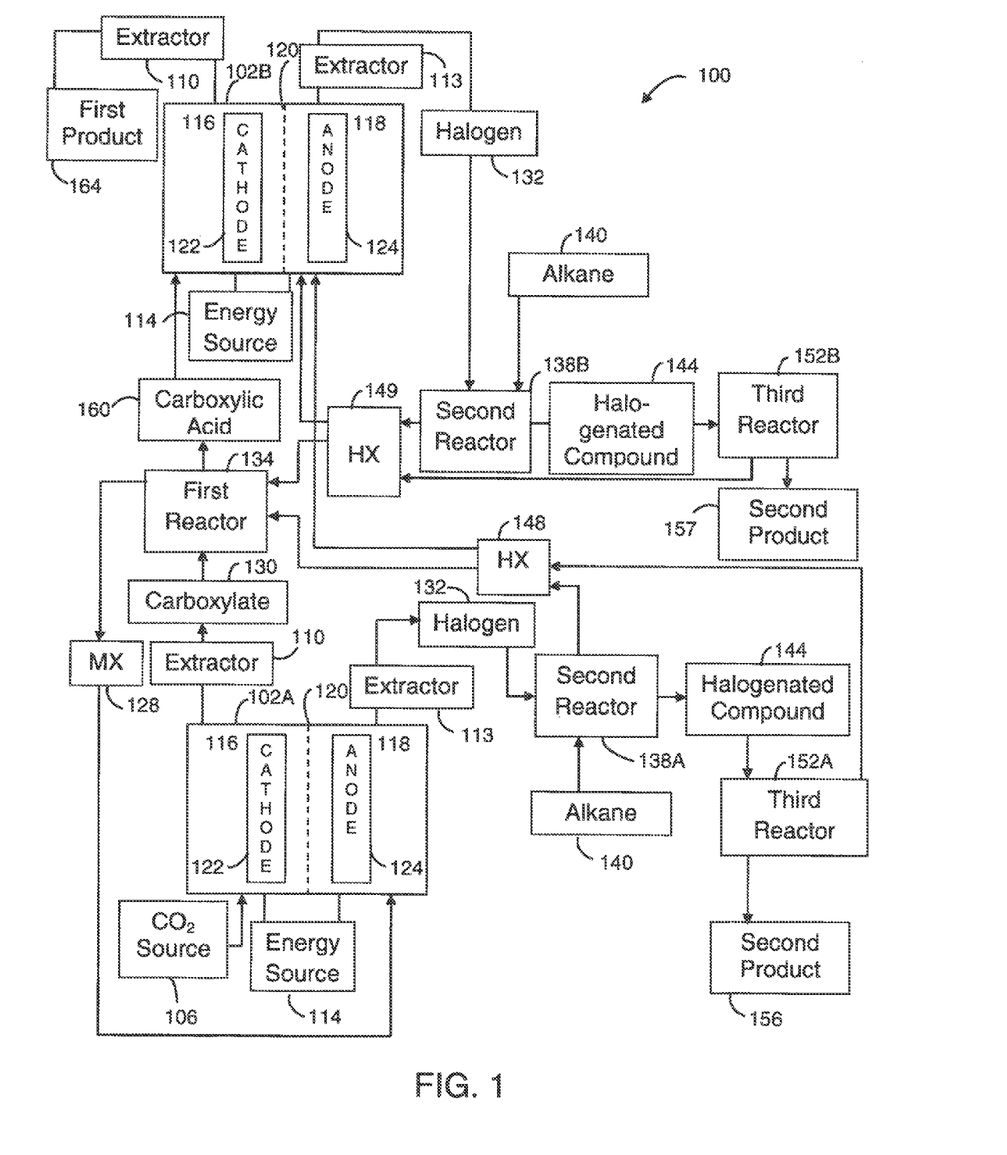
FIG. 1 is a block diagram of a system in accordance with an embodiment of the present disclosure.

Referring to FIG. 1, a block diagram of a system 100 in accordance with an embodiment of the present disclosure is shown. System (or apparatus) 100 may generally include electrochemical cells, such as a first electrochemical cell 102A and a second electrochemical cell 102B, which may also be referred as a container, electrolyzer, or cell. Electrochemical cells 102A and 102B may be implemented as a divided cells. The divided cells may be divided electrochemical cells and/or a divided photo-electrochemical cells. Electrochemical cells 102A and 102B may include a first region 116 and a second region 118. First region 116 and second region 118 may refer to a compartment, section, or generally enclosed space, and the like without departing from the scope and intent of the present disclosure. First region 116 may include a cathode 122. Second region 118 may include an anode 124. First region 116 may include a catholyte whereby carbon dioxide from carbon dioxide source 106 is included in the catholyte. Second region 118 may include an anolyte which may include an MX 128 where M is at least one cation and X is selected from a group consisting of F, Cl, Br, I and mixtures thereof. An energy source 114 may generate an electrical potential between the anode 124 and the cathode 122. The electrical potential may be a DC voltage. Energy source 114 may be configured to supply a variable voltage or constant current to electrochemical cell 102. Separator 120 may selectively control a flow of ions between the first region 116 and the second region 118. Separator 120 may include an ion conducting membrane or diaphragm material.

A cation, as used above, refers to a positively charged species including ions such as Li, Na, K, Cs, Be, Mg, Ca, hydrogen ions, tetraalkyl ammonium ions such as tetrabutylammonium, tetraethylammonium, and tetraalkylphosphonium ions such as tetrabutylphosphonium, tetraethylphosphonium, and in general, $R_1R_2R_3R_4N$ or $R_1R_2R_3R_4P$ where $R_1$ to $R_4$ are independently alkyl, cycloalkyl, branched alkyl, and aryl.

First electrochemical cell 102A is generally operational to reduce carbon dioxide in the first region 116 to a first product recoverable from the first region 116, such as a carboxylate 130 or carboxylate salt while producing a halogen 132 recoverable from the second region 118.

Carbon dioxide source 106 may provide carbon dioxide to the first region 116 of first electrochemical cell 102A. In some embodiments, the carbon dioxide is introduced directly into the region 116 containing the cathode 122. It is contemplated that carbon dioxide source may include a source of a mixture of gases in which carbon dioxide has been filtered or separated from the gas mixture.

In one embodiment, carbon dioxide may be reduced to an oxalate salt at the cathode 122 of the first electrochemical cell 102A while bromine is produced at the anode 124. The two feeds for the electrochemical cell 102A first region are carbon dioxide and a bromide salt such as LiBr, NaBr, KBr, $MgBr_2$, alkylammonium bromide, tetraalkylammonium salts such as tetramethylammonium bromide, tetraethylammonium bromide, tetrabutylammonium bromide, choline bromide, benzyltrimethylammonium bromide, and butyltrimethylammonium bromide. Oxalate salt produced at cathode 122 of the first electrochemical cell 102A may be tetrabutylammonium oxalate. However, other organic salts may be produced to include formates, glyoxylates, glycolates, and acetates, depending on the solvent utilized. While any solvent or any mix of solvents may be used, aprotic solvents such as propylene carbonate may be preferred. A separator 120 may be utilized to minimize or prevent oxidation of the first region 116 product and to minimize or prevent mixing of the anode 124 and cathode 122 products. Separator 120 may be a cation exchange membrane, such as Nafion, or a micro or nanoporous diaphram. Electrochemical cell 102A may be operated in a temperature range from 0° C. to 150° C. Temperatures above 60° C. are preferred for production of gas phase $Br_2$. Electrochemical cell 102A may be operated in a pressure range from 1 to 200 atmospheres, with 1 to 10 atmospheres preferred.

It is contemplated that each electrochemical cell, 102A and 102B, may include a first product extractor 110 and second product extractor 113. Product extractors 110, 113 may implement an organic product and/or inorganic product extractor. First product extractor 110 is generally operational to extract (separate) a product from the first region 116. Second product extractor 113 may extract the second product from the second region 118. It is contemplated that first product extractor and/or second product extractor may be implemented with electrochemical cells 102A and 102B, or may be remotely located from the electrochemical cells 102A 102B. Additionally, it is contemplated that first product extractor and/or second product extractor may be implemented in a variety of mechanisms and to provide desired separation methods, such as fractional distillation, without departing from the scope and intent of the present disclosure. It is further contemplated that extracted product may be presented through a port of the system 100 for subsequent storage and/or consumption by other devices and/or processes.

An anode side of the reaction occurring in the second region 118 of first electrochemical cell 102A may include a recycled reactant of MX. Recycled reactant may include an halide salt which may be a byproduct of a reaction of first reactor 134. For example, the recycled reactant may include MX where where M is at least one alkali metal and X is selected from a group consisting of F, Cl, Br, I and mixtures thereof. M may include H, Li, Na, K, Cs, Mg, Ca, or other metal, or $R_1R_2R_3R_4P^+$, $R_1R_2R_3R_4N^+$—where each R is independently alkyl, branched alkyl, cycloalkyl, or aryl—or a cation; and X is F, Cl, Br, I, or an anion; and mixtures thereof. The anode side of the reaction may produce a halogen 132 which may be presented to second reactor 138A.

System 100 may include second reactor 138A which may receive halogen 132 produced by the second region 118 of first electrochemical cell 102A. Second reactor 138A may react halogen 132 with an alkane or aromatic compound or other carbon compounds that can be partially oxidized with a halogen or mixtures thereof 140 to produce a halogenated compound 144 and HX 148. HX 148 may be another recycled reactant which may be recycled back to the second region 118 as an input feed to the second region 118 of second electrochemical cell 102B and as an input of first reactor 134.

In one embodiment, the alkane 140 may be ethane and second reactor 138A may produce bromoethane. While selectivity for 1-bromoethane is generally greater than 85%, some dibromoethane may also be produced. The dibromoethane may be sold as a separate product, converted to a secondary product such as acetylene, recycled back to the secondary reactor 138A in order to improve selectivity for 1-bromoethane, and/or catalytically converted into 1-bromoethane. HBr will be co-produced with bromoethane and may be recycled back to first reactor 134 or the second region 118 of electrochemical cell 102B. In another embodiment, the aromatic compound may be ethylbenzene which may be brominated to make bromoethylbenzene and HBr.

Halogenated compound 144 may be fed to third reactor 152A. Third reactor 152A may perform a dehydrohalogenation reaction or another chemical reaction of halogenated compound 144 to produce a second product 156. In one embodiment, halogen may refer to $Br_2$ which may react with ethane to produce bromoethane. The dehydrohalogenation reaction of bromoethane may produce ethylene and HBr. The dehydrohalogenation reaction of dibromoethane or dichloroethane may produce acetylene. The dehydrohalogenation of bromopropane may produce propylene. The dehydrohalogenation of bromobutane may produce 1-butene, 2-butene, butadiene, or a mix thereof. The dehydrohalogenation of bromoisobutane or iodoisobutane may produce isobutylene. The dehydrohalogenation reaction of bromoethylbenzene may produce styrene.

First reactor 134 may receive an input feed of carboxylate 130 or carboxylate salt along with recycled input feed of HX 148 to produce carboxylic acid 160. Second electrochemical cell 102B may receive carboxylic acid 160 as a catholyte feed to the first region 116 of the second electrochemical cell 102B. An anode side of the reaction occurring in the second region 118 of second electrochemical cell 102B may include a recycled reactant of HX 149. Recycled reactant may include a hydrogen halide and may include byproducts of at least one second reactor 138A, 138B, and third reactor 152A, 152B.

A cathode reaction of the first region 116 may produce a first product 164 recoverable from the first region 116 of the second electrochemical cell 102B after extractor 110. First product may include at least one of another carboxylic acid, an aldehyde, a ketone, a glycol, or an alcohol. Additional examples of first product 164 may include glyoxylic acid, glyoxal, glycolic acid, glycolaldehyde, acetic acid, acetaldehyde, ethanol, ethane, ethylene or ethylene glycol. An anode reaction of the second region 118 of the second electrochemical cell 102B may produce a halogen 132. Halogen may include $Br_2$ and may be fed to second reactor 138B.

In one embodiment, oxalic acid may be produced by first reactor 134 and first region 116 of second electrochemical cell 102B may reduce the oxalic acid to monoethylene glycol while HBr is oxidized to $Br_2$ in the second region 118. Catholyte of first region 116 may preferably utilize water as solvent, but may include a non-aqueous solvent or mix of solvents. The electrolyte in the cathode compartment is preferably an acid such as HBr, HCl, HI, HF, or $H_2SO_4$, but may include any mixture of salts or acids. The catholyte pH may be less than 7 and preferably between 1 and 5. A homogenous heterocyclic catalyst may be employed in the catholyte. The anolyte may be solely anhydrous gas-phase HBr or HCl or may include a liquid solvent, such as water, in which HBr or HCl is dissolved. In the case of a liquid anolyte, the HBr anolyte concentration may be in the range of 5 wt % to 50 wt %, more preferably in the range of 10 wt % to 40 wt %, and more preferably in the 15 wt % to 30 wt % range, with a corresponding 2 to 30 wt % bromine content as $HBr_3$ in the solution phase. The HBr content in the anolyte solution may control the anolyte solution conductivity, and thus the anolyte region IR voltage drop. If the anode is run with gas phase HBr, then HBr concentrations may approach 100% by wt % and may be run in anhydrous conditions. The cell temperature may range from 10° C. to 100° C., but temperatures less than 60° C. are preferred to produce $Br_2$ in the liquid phase.

Second reactor 138B may react halogen 132 with a carbon compound 140, as described above, to produce a halogenated compound 144 and HX 149. HX 149 may be another recycled reactant which may be recycled back to the second region 118 as an input feed to the second region 118 of second electrochemical cell 102B and as an input of first reactor 134. Halogenated compound 144 may be fed to third reactor 152B.

Third reactor 152A may perform a dehydrohalogenation reaction or another chemical reaction of halogenated compound 144 to produce a second product 157. Second product 157 may include an alkene, alkyne, alcohol, aldehyde, ketone, or longer-chain alkane. It is contemplated that the reaction may occur at elevated temperatures and may include the use of a metal or metal oxide catalyst to reduce the thermal energy required. Temperature ranges for the reaction are from 25° C. to 1,000° C., with temperatures below 500° C. preferable.

In one embodiment, halogen may refer to $Br_2$ which may react with ethane to produce bromoethane. The dehydrohalogenation reaction of bromoethane may produce ethylene and HBr. It is contemplated that a diverter, or diverter valve may be inserted in the feed for the HX 148 feed between the second reactor 138A, 138B and the third reactors 152A and 152B and an input of the first reactor 134 and the input to the second region 118 of the second electrochemical cell 102B to ensure a proper amount of HX is supplied to each of the first reactor 134 and the input to the second region 118 of the second electrochemical cell 102B.

Figure 2:
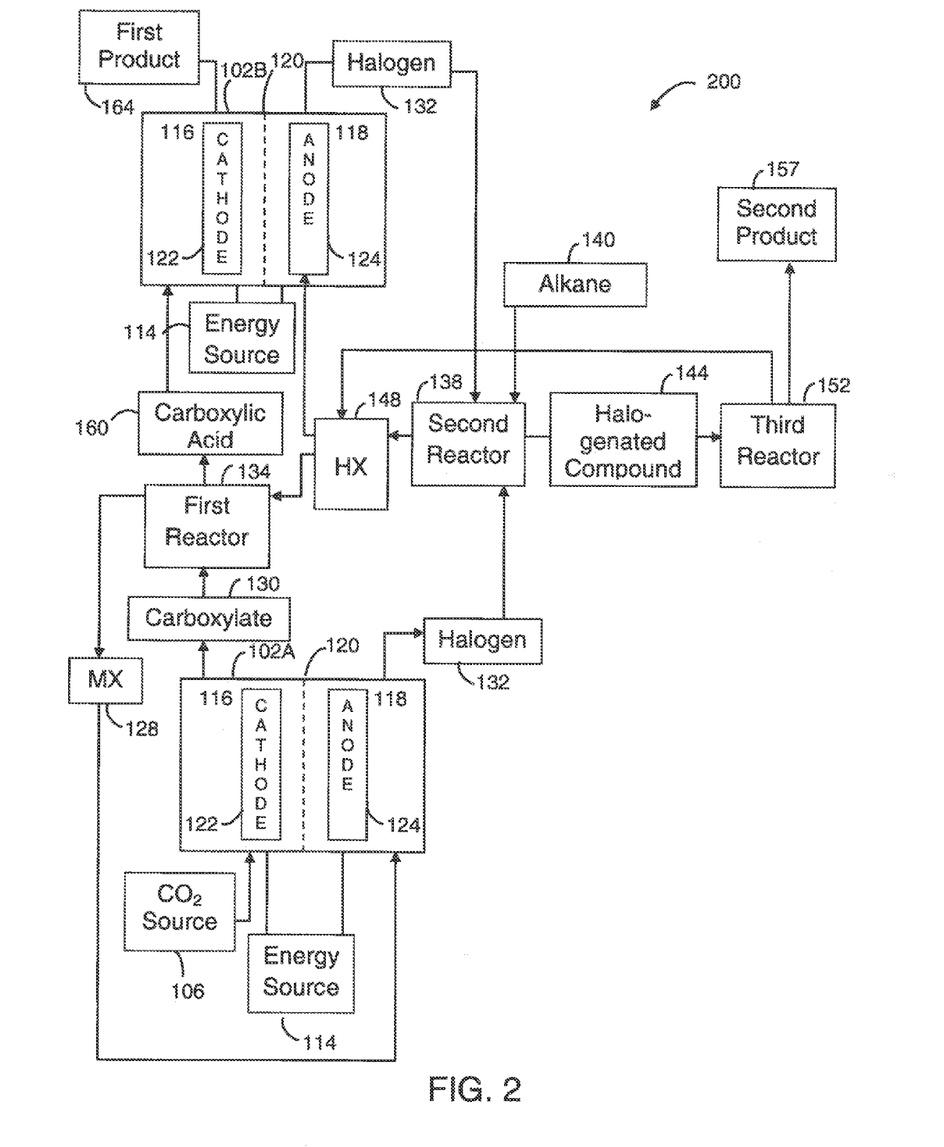
FIG. 2 is a block diagram of a system in accordance with another embodiment of the present disclosure.
Figure 3:
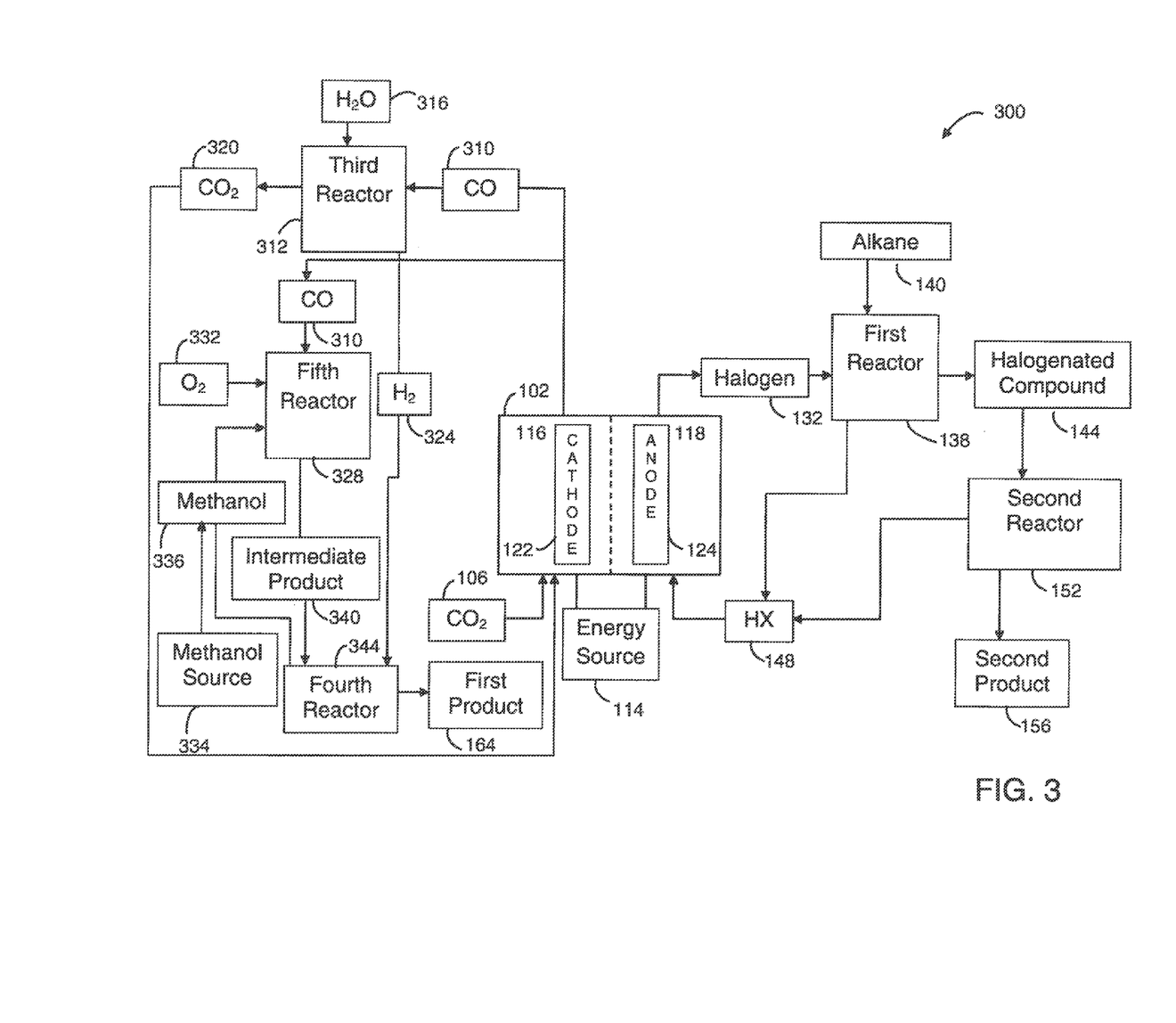
FIG. 3 is a block diagram of a system in accordance with an additional embodiment of the present disclosure.

Referring to FIG. 2, a block diagram of a system 200 in accordance with another embodiment of the present disclosure is shown. System 200 may be substantially similar to system 100 of FIG. 1. However, system 200 may include a second reactor 138 implemented as a single reactor and third reactor 152 implemented as a single reactor, rather than as two or more reactors as shown in system 100 of FIG. 1. It is contemplated that system 200 may also include a diverter, or diverter valve inserted in the feed for the HX 148 feed between the second reactor 138 and the third reactor 152 and an input of the first reactor 134 and the input to the second region 118 of the second electrochemical cell 102B to ensure a proper amount of HX is supplied to each of the first reactor 134 and the input to the second region 118 of the second electrochemical cell 102B. Second product 157 from third reactor 152 may include an alkene, alkyne, alcohol, aldehyde, ketone, or longer-chain alkane. Referring to FIG. 3, a block diagram of a system 300 in accordance with an additional embodiment of the present disclosure is shown. System 300 may include a single electrochemical cell 102. Carbon dioxide source 106 may provide carbon dioxide to the first region 116 of first electrochemical cell 102. Cathode reaction may reduce carbon dioxide to a carbon dioxide reduction product such as CO 310. An anode side of the reaction occurring in the second region 118 of first electrochemical cell 102 may include a recycled reactant of HX where H is hydrogen and X is selected from a group consisting of F, Cl, Br, I and mixtures thereof. The anode side of the reaction may produce a halogen 132 which may be provided to first reactor 138.

First reactor 138 may react halogen 132, such as $Br_2$ with a compound 140, as described above, such as ethane, to produce a halogenated compound 144, such as bromoethane and HX 148, such as HBr. HX 148 may be recycled reactant which may be recycled back to the second region 118 of electrochemical cell 102. Halogenated compound 144 may be fed to second reactor 152 to produce a second product 156. Second product 156 may include an alkene, alkyne, alcohol, aldehyde, ketone, or longer-chain alkane, such as ethylene.

CO 310 may be fed to third reactor 312. Third reactor 312 may perform a water gas shift reaction and react CO 310 and water 316 to produce carbon dioxide 320 and $H_2$ 324. Carbon dioxide 320 may be recycled back to the input of the first region 116 of electrochemical cell 102. $H_2$ 324 may be fed to fourth reactor 344. Fifth reactor 328 may receive CO 310 from the first region 116 of electrochemical cell 102 and may receive an $O_2$ 332 input and a methanol input 336 supplied by a methanol source 334 to produce an intermediate product 340. In one embodiment, intermediate product 340 may be dimethyl oxalate. The intermediate product 340, such as dimethyl oxalate, may be fed to fourth reactor 344. Fourth reactor 344 may react intermediate product 340 with $H_2$ 324 reduce the intermediate product 340 to produce a first product 164 and a methanol 336 byproduct which is recycled back to reactor 328. First product 164 may include an glyoxylic acid, glyoxal, glycolic acid, glycolaldehyde, acetic acid, acetaldehyde, ethanol, ethane, ethylene, or ethylene glycol.

Figure 4:
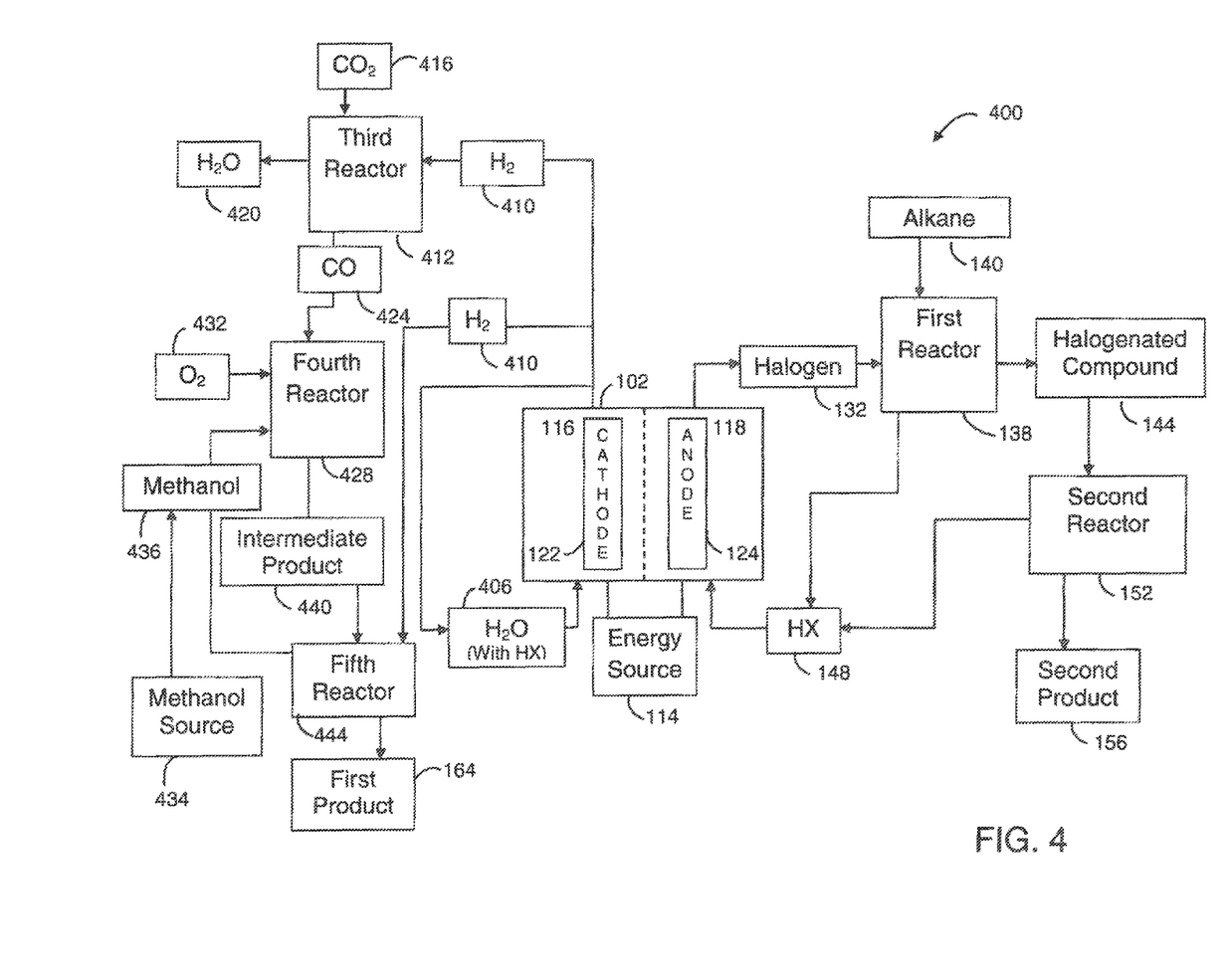
FIG. 4 is a block diagram of a system in accordance with another additional embodiment of the present disclosure.

Referring to FIG. 4, a block diagram of a system 400 in accordance with another additional embodiment of the present disclosure is shown. System 400 may include a single electrochemical cell 102. A water source 406, which may include HX where H is hydrogen and X is selected from a group consisting of F, Cl, Br, I and mixtures thereof, may be provided to the first region 116 of electrochemical cell 102. Water with HX 406 may be produced at the first region 116 and recycled back to an input of the first region 116. Cathode reaction may also produce $H_2$ 410. An anode side of the reaction occurring in the second region 118 of first electrochemical cell 102 may include a recycled reactant of HX 148. The anode side of the reaction may produce a halogen 132 which may be provided to first reactor 138.

First reactor 138 may react halogen 132, such as $Br_2$ with a compound 140, as described above, such as ethane, to produce a halogenated compound 144, such as bromoethane and HX 148, such as HBr. HX 148 may be a recycled reactant which may be recycled back to the second region 118 of electrochemical cell 102. Halogenated compound 144 may be fed to second reactor 152 to produce a second product 156. Second product 156 may include an alkene, alkyne, alcohol, aldehyde, ketone, or longer-chain alkane, such as ethylene.

$H_2$ 410 may be fed to third reactor 412. Reactor 412 may perform a reverse water gas shift reaction and react $H_2$ 410 and carbon dioxide 316 to produce water 420 and CO 424. Water may be recycled to an input of the first region 116 of electrochemical cell. CO 424 may be fed to fourth reactor 428. Fourth reactor 428 may react CO 424 with $O_2$ 432 and methanol 436 supplied from methanol source 434 to produce an intermediate product 440. Intermediate product 440 may be dimethyl oxalate. The intermediate product 440, such as dimethyl oxalate, may be fed to fifth reactor 444. Reactor 444 may react intermediate product 440 with $H_2$ 410 from second region 116 of electrochemical cell 102 to reduce the intermediate product to produce a first product 164 and a methanol 336 byproduct which is recycled back to fourth reactor 428. First product 164 may include an glyoxylic acid, glyoxal, glycolic acid, glycolaldehyde, acetic acid, acetaldehyde, ethanol, ethane, ethylene, or ethylene glycol.

In addition to the systems 300, 400 of FIG. 3 and FIG. 4, another system to produce ethylene glycol may include producing oxalate in a first electrochemical cell from carbon dioxide and $Br_2$ from MBr, where M is a cation. A second electrochemical cell may utilize HBr at the anode. The second electrochemical cell may produce $H_2$ at the cathode and $Br_2$ at the anode. $Br_2$ may be used in the thermal processes to make HBr, which may be recycled to the HBr electrochemical cell and also used to acidify oxalate to oxalic acid. The oxalic acid may be reduced to ethylene glycol in a thermal process utilizing $H_2$ from the HBr electrolyzer. Oxalic acid may also be reduced to glyoxylic acid, glycolic acid, glyoxal, glycolaldehyde, acetic acid, acetaldehyde, and/or ethanol.

It is contemplated that a receiving feed may include various mechanisms for receiving a supply of a product, whether in a continuous, near continuous or batch portions.

It is further contemplated that the structure and operation of the electrochemical cell 102, which includes electrochemical cells 102A and 102B, and 102 in FIGS. 1-4, may be adjusted to provide desired results. For example, the electrochemical cell 102 may operate at higher pressures, such as pressure above atmospheric pressure which may increase current efficiency and allow operation of the electrochemical cell at higher current densities.

Additionally, the cathode 122 and anode 124 may include a high surface area electrode structure with a void volume which may range from 30% to 98%. The electrode void volume percentage may refer to the percentage of empty space that the electrode is not occupying in the total volume space of the electrode. The advantage in using a high void volume electrode is that the structure has a lower pressure drop for liquid flow through the structure. The specific surface area of the electrode base structure may be from 2 $cm^2/cm^3$ to 500 $cm^2/cm^3$ or higher. The electrode specific surface area is a ratio of the base electrode structure surface area divided by the total physical volume of the entire electrode. It is contemplated that surface areas also may be defined as a total area of the electrode base substrate in comparison to the projected geometric area of the current distributor/conductor back plate, with a preferred range of 2× to 1000× or more. The actual total active surface area of the electrode structure is a function of the properties of the electrode catalyst deposited on the physical electrode structure which may be 2 to 1000 times higher in surface area than the physical electrode base structure.

Cathode 122 may be selected from a number of high surface area materials to include copper, stainless steels, transition metals and their alloys and oxides, carbon, and silicon, which may be further coated with a layer of material which may be a conductive metal or semiconductor. The base structure of cathode 122 may be in the form of fibrous, reticulated, or sintered powder materials made from metals, carbon, or other conductive materials including polymers. The materials may be a very thin plastic screen incorporated against the cathode side of the membrane to prevent the membrane 120 from directly touching the high surface area cathode structure. The high surface area cathode structure may be mechanically pressed against a cathode current distributor backplate, which may be composed of material that has the same surface composition as the high surface area cathode.

In addition, cathode 122 may be a suitable conductive electrode, such as Al, Au, Ag, Bi, C, Cd, Co, Cr, Cu, Cu alloys (e.g., brass and bronze), Ga, Hg, In, Mo, Nb, Ni, $NiCo_2O_4$, Ni alloys (e.g., Ni 625, NiHX), Ni—Fe alloys, Pb, Pd alloys (e.g., PdAg), Pt, Pt alloys (e.g., PtRh), Rh, Sn, Sn alloys (e.g., SnAg, SnPb, SnSb), Ti, V, W, Zn, stainless steel (SS) (e.g., SS 2205, SS 304, SS 316, SS 321), austenitic steel, ferritic steel, duplex steel, martensitic steel, Nichrome (e.g., NiCr 60:16 (with Fe)), elgiloy (e.g., Co—Ni—Cr), degenerately doped p-Si, degenerately doped p-Si:As, degenerately doped p-Si: B, degenerately doped n-Si, degenerately doped n-Si:As, and degenerately doped n-Si:B. These metals and their alloys may also be used as catalytic coatings on the various metal substrates. Other conductive electrodes may be implemented to meet the criteria of a particular application. For photo-electrochemical reductions, cathode 122 may be a p-type semiconductor electrode, such as p-GaAs, p-GaP, p-InN, p-InP, p-CdTe, p-GaInP$_2$ and p-Si, or an n-type semiconductor, such as n-GaAs, n-GaP, n-InN, n-InP, n-CdTe, n-GaInP$_2$ and n-Si. Other semiconductor electrodes may be implemented to meet the criteria of a particular application including, but not limited to, CoS, MoS$_2$, TiB, WS$_2$, SnS, Ag$_2$S, CoP$_2$, Fe$_3$P, Mn$_3$P$_2$, MoP, Ni$_2$Si, MoSi$_2$, WSi2, CoSi$_2$, Ti$_4$O$_7$, SnO$_2$, GaAs, GaSb, Ge, and CdSe.

Catholyte may include a pH range from 1 to 12 when an aqeuous solvent is employed, preferably from pH 4 to pH 10. The selected operating pH may be a function of any catalysts utilized in operation of the electrochemical cell 102. Preferably, catholyte and catalysts may be selected to prevent corrosion at the electrochemical cell 102. Catholyte may include homogeneous catalysts. Homogeneous catalysts are defined as aromatic heterocyclic amines and may include, but are not limited to, unsubstituted and substituted pyridines and imidazoles. Substituted pyridines and imidazoles may include, but are not limited to mono and disubstituted pyridines and imidazoles. For example, suitable catalysts may include straight chain or branched chain lower alkyl (e.g., Cl-C10) mono and disubstituted compounds such as 2-methylpyridine, 4-tertbutyl pyridine, 2,6 dimethylpyridine (2,6-lutidine); bipyridines, such as 4,4'-bipyridine; amino-substituted pyridines, such as 4-dimethylamino pyridine; and hydroxylsubstituted pyridines (e.g., 4-hydroxy-pyridine) and substituted or unsubstituted quinoline or isoquinolines. The catalysts may also suitably include substituted or unsubstituted dinitrogen heterocyclic amines, such as pyrazine, pyridazine and pyrimidine. Other catalysts generally include azoles, imidazoles, indoles, oxazoles, thiazoles, substituted species and complex multi-ring amines such as adenine, pterin, pteridine, benzimidazole, phenonthroline and the like.

The catholyte may include an electrolyte. Catholyte electrolytes may include alkali metal bicarbonates, carbonates, sulfates, phosphates, borates, and hydroxides. The electrolyte may comprise one or more of Na$_2$SO$_4$, KCl, NaNO$_3$, NaCl, NaF, NaClO$_4$, KClO$_4$, K$_2$SiO$_3$, CaCl$_2$, a guanidinium cation, an H cation, an alkali metal cation, an ammonium cation, an alkylammonium cation, a tetraalkyl ammonium cation, a halide anion, an alkyl amine, a borate, a carbonate, a guanidinium derivative, a nitrite, a nitrate, a phosphate, a polyphosphate, a perchlorate, a silicate, a sulfate, and a hydroxide. In one embodiment, bromide salts such as NaBr or KBr may be preferred.

The catholyte may further include an aqueous or non-aqueous solvent. An aqueous solvent may include greater than 5% water. A non-aqueous solvent may include as much as 5% water. A solvent may contain one or more of water or a non-aqueous solvent. Representative solvents include methanol, ethanol, acetonitrile, propylene carbonate, ethylene carbonate, dimethyl carbonate, diethyl carbonate, dimethylsulfoxide, dimethylformamide, acetonitrile, acetone, tetrahydrofuran, N,N-dimethylacetaminde, dimethoxyethane, diethylene glycol dimethyl ester, butyrolnitrile, 1,2-difluorobenzene, y-butyrolactone, N-methyl-2-pyrrolidone, sulfolane, 1,4-dioxane, nitrobenzene, nitromethane, acetic anhydride, hexane, heptane, octane, kerosene, toluene, xylene, ionic liquids, and mixtures thereof.

In one embodiment, a catholyte/anolyte flow rate may include a catholyte/anolyte cross sectional area flow rate range such as 2-3,000 gpm/ft$^2$ or more (0.0076-11.36 m$^3$/m$^2$). A flow velocity range may be 0.002 to 20 ft/sec (0.0006 to 6.1 m/sec). Operation of the electrochemical cell catholyte at a higher operating pressure allows more dissolved carbon dioxide to dissolve in the aqueous solution. Typically, electrochemical cells can operate at pressures up to about 20 to 30 psig in multi-cell stack designs, although with modifications, the electrochemical cells may operate at up to 100 psig. The electrochemical cell may operate anolyte at the same pressure range to minimize the pressure differential on a separator 120 or membrane separating the two regions. Special electrochemical designs may be employed to operate electrochemical units at higher operating pressures up to about 60 to 100 atmospheres or greater, which is in the liquid CO$_2$ and supercritical CO$_2$ operating range.

In another embodiment, a portion of a catholyte recycle stream may be separately pressurized using a flow restriction with backpressure or using a pump, with CO$_2$ injection, such that the pressurized stream is then injected into the catholyte region of the electrochemical cell which may increase the amount of dissolved CO$_2$ in the aqueous solution to improve the conversion yield. In addition, micro-bubble generation of carbon dioxide can be conducted by various means in the catholyte recycle stream to maximize carbon dioxide solubility in the solution.

Catholyte may be operated at a temperature range of −10 to 95° C., more preferably 5-60° C. The lower temperature will be limited by the catholytes used and their freezing points. In general, the lower the temperature, the higher the solubility of CO$_2$ in an aqueous solution phase of the catholyte, which would help in obtaining higher conversion and current efficiencies. The drawback is that the operating electrochemical cell voltages may be higher, so there is an optimization that would be done to produce the chemicals at the lowest operating cost. In addition, the catholyte may require cooling, so an external heat exchanger may be employed, flowing a portion, or all, of the catholyte through the heat exchanger and using cooling water to remove the heat and control the catholyte temperature.

Anolyte operating temperatures may be in the same ranges as the ranges for the catholyte, and may be in a range of 0° C. to 95° C. In addition, the anolyte may require cooling, so an external heat exchanger may be employed, flowing a portion, or all, of the anolyte through the heat exchanger and using cooling water to remove the heat and control the anolyte temperature.

Electrochemical cells may include various types of designs. These designs may include zero gap designs with a finite or zero gap between the electrodes and membrane, flow-by and flow-through designs with a recirculating catholyte electrolyte utilizing various high surface area cathode materials. The electrochemical cell may include flooded co-current and counter-current packed and trickle bed designs with the various high surface area cathode materials. Also, bipolar stack cell designs and high pressure cell designs may also be employed for the electrochemical cells.

Anode electrodes may be the same as cathode electrodes or different. Anode 124 may include electrocatalytic coatings applied to the surfaces of the base anode structure. Anolytes may be the same as catholytes or different. Anolyte electrolytes may be the same as catholyte electrolytes or different.

Anolyte may comprise solvent. Anolyte solvent may be the same as catholyte solvent or different. For example, for HBr, acid anolytes, and oxidizing water generating oxygen, the preferred electrocatalytic coatings may include precious metal oxides such as ruthenium and iridium oxides, as well as platinum and gold and their combinations as metals and oxides on valve metal substrates such as titanium, tantalum, zirconium, or niobium. For bromine and iodine anode chemistry, carbon and graphite are particularly suitable for use as anodes. Polymeric bonded carbon material may also be used. For other anolytes, comprising alkaline or hydroxide electrolytes, anodes may include carbon, cobalt oxides, stainless steels, transition metals, and their alloys and combinations. High surface area anode structures that may be used which would help promote the reactions at the anode surfaces. The high surface area anode base material may be in a reticulated form composed of fibers, sintered powder, sintered screens, and the like, and may be sintered, welded, or mechanically connected to a current distributor back plate that is commonly used in bipolar electrochemical cell assemblies. In addition, the high surface area reticulated anode structure may also contain areas where additional applied catalysts on and near the electrocatalytic active surfaces of the anode surface structure to enhance and promote reactions that may occur in the bulk solution away from the anode surface such as the reaction between bromine and the carbon based reactant being introduced into the anolyte. The anode structure may be gradated, so that the density of the may vary in the vertical or horizontal direction to allow the easier escape of gases from the anode structure. In this gradation, there may be a distribution of particles of materials mixed in the anode structure that may contain catalysts, such as metal halide or metal oxide catalysts such as iron halides, zinc halides, aluminum halides, cobalt halides, for the reactions between the bromine and the carbon-based reactant. For other anolytes comprising alkaline, or hydroxide electrolytes, anodes may include carbon, cobalt oxides, stainless steels, and their alloys and combinations.

Separator 120, also referred to as a membrane, between a first region 118 and second region 118, may include cation ion exchange type membranes. Cation ion exchange membranes which have a high rejection efficiency to anions may be preferred. Examples of such cation ion exchange membranes may include perfluorinated sulfonic acid based ion exchange membranes such as DuPont Nafion® brand unreinforced types N117 and N120 series, more preferred PTFE fiber reinforced N324 and N424 types, and similar related membranes manufactured by Japanese companies under the supplier trade names such as AGC Engineering (Asahi Glass) under their trade name Flemion®. Other multi-layer perfluorinated ion exchange membranes used in the chlor alkali industry may have a bilayer construction of a sulfonic acid based membrane layer bonded to a carboxylic acid based membrane layer, which efficiently operates with an anolyte and catholyte above a pH of about 2 or higher. These membranes may have a higher anion rejection efficiency. These are sold by DuPont under their Nafion® trademark as the N900 series, such as the N90209, N966, N982, and the 2000 series, such as the N2010, N2020, and N2030 and all of their types and subtypes. Hydrocarbon based membranes, which are made from of various cation ion exchange materials can also be used if the anion rejection is not as desirable, such as those sold by Sybron under their trade name Ionac®, AGC Engineering (Asahi Glass) under their Selemion® trade name, and Tokuyama Soda, among others on the market. Ceramic based membranes may also be employed, including those that are called under the general name of NASICON (for sodium super-ionic conductors) which are chemically stable over a wide pH range for various chemicals and selectively transports sodium ions, the composition is $Na_{1+x}Zr_2Si_xP_3-xO_{12}$, and well as other ceramic based conductive membranes based on titanium oxides, zirconium oxides and yttrium oxides, and beta aluminum oxides. Alternative membranes that may be used are those with different structural backbones such as polyphosphazene and sulfonated polyphosphazene membranes in addition to crown ether based membranes. Preferably, the membrane or separator is chemically resistant to the anolyte and catholyte and operates at temperatures of less than 600 degrees C., and more preferably less than 500 degrees C.

A rate of the generation of reactant formed in the anolyte compartment from the anode reaction, such as the oxidation of HBr to bromine, is contemplated to be proportional to the applied current to the electrochemical cell 102B. The anolyte product output in this range can be such that the output stream contains little or no free bromine in the product output, or it may contain unreacted bromine. The operation of the extractor and its selected separation method, for example fractional distillation, the actual products produced, and the selectivity may be adjusted to obtain desired characteristics. Any of the unreacted components would be recycled to the second region 118.

Similarly, a rate of the generation of the formed electrochemical carbon dioxide reduction product, such as CO, is contemplated to be proportional to the applied current to electrochemical cells 102, 102A, and 102B. The rate of the input or feed of the carbon dioxide source 106 into the first region 116 should be fed in a proportion to the applied current. The cathode reaction efficiency would determine the maximum theoretical formation in moles of the carbon dioxide reduction product. It is contemplated that the ratio of carbon dioxide feed to the theoretical moles of potentially formed carbon dioxide reduction product would be in a range of 100:1 to 2:1, and preferably in the range of 50:1 to 5:1, where the carbon dioxide is in excess of the theoretical required for the cathode reaction. The carbon dioxide excess would then be separated and recycled back to the first region 116.

In the present disclosure, the methods disclosed may be implemented as sets of instructions or software readable by a device. Further, it is understood that the specific order or hierarchy of steps in the methods disclosed are examples of exemplary approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed is:

1. A method for co-producing a first product and a second product, the method comprising the steps of:
   contacting a first region of a first electrochemical cell having an cathode with a catholyte comprising carbon dioxide;

contacting a second region of a first electrochemical cell having an anode with an anolyte comprising a MX where M is at least one cation and X is selected from a group consisting of F, Cl, Br, I, and mixtures thereof;

applying an electrical potential between the anode and the cathode sufficient to produce M-carboxylate recoverable from the first region of the first electrochemical cell and a halogen recoverable from the second region of the first electrochemical cell;

reacting the M-carboxylate with HX via a secondary reactor to produce a carboxylic acid and MX, the MX being recycled to an input of the second region of the first electrochemical cell;

contacting a first region of a second electrochemical cell having a cathode with a catholyte comprising the carboxylic acid;

contacting a second region of a second electrochemical cell having an anode with an anolyte comprising HX;

applying an electrical potential between the anode of the second electrochemical cell and the cathode of the second electrochemical cell sufficient to produce at least one of another carboxylic acid, an aldehyde, a ketone, a glycol or an alcohol recoverable from the first region of the second electrochemical cell and a halogen recoverable from the second region of the second electrochemical cell;

reacting the halogen from the second region of the first electrochemical cell and from the second region of the second electrochemical cell with an alkane, aromatic compound, or other carbon compound to produce a halogenated compound and HX, the HX being recycled back to the second region of the second electrochemical cell and to the input of the secondary reactor; and reacting the halogenated compound via at least one reactor to produce at least one of an alkene, alkyne, alcohol, phenol, aldehyde, ketone, unsaturated carbon compound, or longer-chain alkane, and HX, the HX being recycled back to the second region of the second electrochemical cell and to the input of the secondary reactor.

2. The method according to claim 1, wherein the halogen includes at least one of $F_2$, $Cl_2$, $Br_2$, or $I_2$.

3. The method according to claim 1, wherein the halogen is reacted with at least one of methane, ethane, propane, butane, isobutane, benzene, toluene, or xylene.

4. The method according to claim 1, wherein the M-carboxylate is M oxalate.

5. The method according to claim 1, wherein at least one of glyoxylic acid, glyoxal, glycolic acid, glycolaldehyde, acetic acid, acetaldehyde, ethanol, ethane, ethylene, or ethylene glycol is recoverable from the first region of the second electrochemical cell.

6. The method according to claim 1, wherein the cathode and the anode of the first electrochemical cell and the cathode and the anode of the second electrochemical cell, are separated by an ion permeable barrier that operates at a temperature less than 600 degrees C.

7. The method according to claim 6, wherein the ion permeable barrier includes one of a polymeric or inorganic ceramic-based ion permeable barrier.

8. The method according to claim 1, wherein the catholyte of the second electrochemical cell is liquid phase and the anolyte of the second electrochemical cell is gas phase.

9. The method according to claim 1, wherein at least one of: the catholyte and the anolyte of the first electrochemical cell; and the catholyte and the anolyte of the second electrochemical cell;

is non-aqueous.

10. The method according to claim 1, wherein reacting the recovered halogen from the second region of the first electrochemical cell and the second region of the second electrochemical cell with an alkane, aromatic compound, or other carbon compound is performed by at least a single reactor.

11. The method according to claim 1, wherein reacting the recovered halogen from the second region of the first electrochemical cell and the second region of the second electrochemical cell with an alkane, aromatic compound, or other carbon compound is performed by at least two reactors.

12. A method for co-producing a first product and a second product, the method comprising the steps of:

applying an electrical potential between a cathode of a first region of a first electrochemical cell, including a catholyte comprising carbon dioxide, and an anode of a second region of a first electrochemical cell, the second region including an anolyte comprising MX, where M is at least one cation and X is selected from a group consisting of F, Cl, Br, I, and mixtures thereof, sufficient to produce M-carboxylate recoverable from the first region of the first electrochemical cell and a halogen recoverable from the second region of the first electrochemical cell;

reacting the M-carboxylate with HX via a secondary reactor to produce a carboxylic acid and MX, the MX being recycled to an input of the second region of the first electrochemical cell;

applying an electrical potential between a cathode of a first region of a second electrochemical cell, including a catholyte comprising the carboxylic acid, and an anode of a second region of a second electrochemical cell, including an anolyte comprising HX, sufficient to produce at least one of another carboxylic acid, an aldehyde, a ketone, a glycol or an alcohol recoverable from the first region of the second electrochemical cell and a halogen recoverable from the second region of the second electrochemical cell;

reacting the halogen from the second region of the first electrochemical cell and from the second region of the second electrochemical cell with an alkane, aromatic compound, or other carbon compound, to produce a halogenated compound and HX, the HX being recycled back to the second region of the second electrochemical cell and to the input of the secondary reactor; and reacting the halogenated compound via at least a third reactor to produce at least one of an alkene, alkyne, alcohol, aldehyde, ketone, or longer-chain alkane, and HX, the HX being recycled back to the second region of the second electrochemical cell and to the input of the secondary reactor.

13. The method according to claim 12, wherein the halogen includes at least one of $F_2$, $Cl_2$, $Br_2$, or $I_2$.

14. The method according to claim 12, wherein the alkane, aromatic compound, or other carbon compound includes at least one of methane, ethane, propane, or butane.

15. The method according to claim 12, wherein the M-carboxylate is M-oxalate.

16. The method according to claim 12, wherein at least one of glyoxylic acid, glyoxal, glycolic acid, glycolaldehyde, acetic acid, acetaldehyde, ethanol, ethane, ethylene, or ethylene glycol is recoverable from the first region of the second electrochemical cell.

17. The method according to claim 12, wherein the cathode and the anode of the first electrochemical cell and the cathode and the anode of the second electrochemical cell, are separated by an ion permeable barrier that operates at a temperature less than 600 degrees C.

18. The method according to claim 17, wherein the ion permeable barrier includes one of a polymeric or inorganic ceramic-based ion permeable barrier.

19. The method according to claim 12, wherein the catholyte of the second electrochemical cell is liquid phase and the anolyte of the second electrochemical cell is gas phase.

20. The method according to claim 12, wherein at least one of:

the catholyte and the anolyte of the first electrochemical cell; and     the catholyte and the anolyte of the second electrochemical cell;

are non-aqueous.

\* \* \* \* \*